United States Patent [19]

Myllymäki

[11] Patent Number: 5,670,944
[45] Date of Patent: Sep. 23, 1997

[54] BODY-HELD MONITORING DEVICE FOR PHYSICAL CONDITION

[76] Inventor: Matti Myllymäki, Sisämaantie 18 A, FIN-02780 Espoo, Finland

[21] Appl. No.: 605,226

[22] PCT Filed: Sep. 13, 1994

[86] PCT No.: PCT/FI94/00401

§ 371 Date: Mar. 8, 1996

§ 102(e) Date: Mar. 8, 1996

[87] PCT Pub. No.: WO95/07652

PCT Pub. Date: Mar. 23, 1995

[30] Foreign Application Priority Data

Sep. 14, 1993 [FI] Finland .................. 934012

[51] Int. Cl.⁶ ................................... G08B 23/00
[52] U.S. Cl. .............. 340/573; 128/687; 128/734; 128/736; 128/774; 128/903; 340/539
[58] Field of Search .................... 340/573, 539, 340/691, 693, 522; 128/903, 782, 774, 736, 734, 690, 687; 364/413.03, 413.04

[56] References Cited

U.S. PATENT DOCUMENTS

| 3,830,228 | 8/1974 | Foner | 128/696 |
|---|---|---|---|
| 4,052,979 | 10/1977 | Scherr et al. | 128/690 |
| 4,202,350 | 5/1980 | Walton | 128/690 |
| 4,425,921 | 1/1984 | Fujisaki et al. | 128/690 |
| 4,625,733 | 12/1986 | Saynajakangas | 128/687 |
| 4,665,928 | 5/1987 | Linial et al. | 128/782 |
| 4,757,453 | 7/1988 | Nasiff | 364/415 |
| 4,819,860 | 4/1989 | Hargrove et al. | 128/668 |
| 4,938,228 | 7/1990 | Righter et al. | 128/690 |
| 4,952,928 | 8/1990 | Carroll et al. | 340/825.54 |
| 4,958,645 | 9/1990 | Cadell et al. | 128/903 |
| 5,025,791 | 6/1991 | Niwa | 128/670 |
| 5,197,489 | 3/1993 | Conlan | 128/782 |

FOREIGN PATENT DOCUMENTS

| 2686497 | 7/1993 | France | 128/690 |
|---|---|---|---|
| 2036552 | 2/1972 | Germany | 340/573 |
| 3613889 | 10/1987 | Germany | 128/690 |
| 4325087 | 2/1994 | Germany | 340/573 |
| 259446 | 9/1992 | Japan | 128/690 |
| 2240392 | 7/1991 | United Kingdom | 340/573 |
| 16636 | 9/1993 | WIPO | 128/690 |

*Primary Examiner*—Thomas Mullen
*Attorney, Agent, or Firm*—Christensen O'Connor Johnson & Kindness PLLC

[57] ABSTRACT

A body-held monitoring device monitors a physical condition and/or a performance condition. A plurality of transducers (3–6) each measure various quantities indicating a physical condition and/or a performance condition. The plurality of transducers includes a multiple detector transducer (4–6) designed by a film technique. The transducers are monitored by means of a microprocessor (9) that provides information indicating the physical condition and/or performance condition of a monitored person in such a manner that a comparison of a plurality of different transducer signals is used to compensate for an anomaly from an individual transducer. A body-held transducer unit (1) has a skin-contacting surface carrying at least some of the transducers, and a wrist-held display and detector unit (2) displays the information indicating a physical condition and/or performance condition by means of a display and/or a sound signal.

7 Claims, 2 Drawing Sheets

BODY-HELD MONITORING DEVICE FOR PHYSICAL CONDITION

FIELD OF THE INVENTION

The present invention relates to a body-held monitoring device for independently observing the physical condition and/or performance condition of a person by means of motoric activity, moisture of the skin, electric conductivity of the skin, surface temperature and heart rate. The anomalous condition data is displayed locally or transmitted by a prior known wireless technique to a remote receiver, which sets off a local alarm and transmits it by a prior known technique to an alarm center. The local display can also be used for monitoring the performance condition of a person regardless of whether anything abnormal has occurred. In this context, the performance condition relates to a condition resulting from physical and mental stress, which is measurable as chemical and physical changes caused by the sympathetic nervous system (e.g. a stress condition).

BACKGROUND OF THE INVENTION

A body-held device, capable of the independent and on-line surveillance of a physical condition/performance condition by means of a plurality (placed in various locations) of transducers in such a manner that the user him- or herself is able to monitor his or her condition, is not yet in sight. Traditionally, the surveillance has been effected by means of heart rate or some other biophysical indicator and, thus, it has not been possible for the user alone to create a general description of physical condition in such a manner that motoric activity and/or biophysical changes in the skin are taken into consideration. It is also prior known to measure a physical condition from the wrist in such a manner that an alarm is automatically transmitted in an abnormal condition, but a problem is how to provide an accurate description for the user him- or herself as well as the surveillance level limited by a low current consumption. It is also prior known to measure the intensity of a human stress by means of a biophysical indicator, but the problem has been the narrowness of an image produced by just a single indicator and, thus, producing a reliable image has required limited measuring conditions.

SUMMARY OF THE INVENTION

An object of the invention is to provide a body-held device, which the user wears continuously for example around the chest, ankle or some other body member suitable for measuring and which monitors a physical condition/performance condition continuously and delivers to its user locally, e.g. by way of a wrist-held display and detector unit, information about a physical or performance condition in such a manner that the user also receives information about an anomalous condition either through a sound signal and/or the display of a wrist unit. An alarm indicating an abnormal condition can also be transmitted in a wireless fashion by using either an emergency phone or a public radiophone network in such a manner that the alarm is provided with location information by using available satellite locating systems. Another object of the invention is to create a device, whereby the user receives information about his or her performance condition, e.g. a stress condition, and is able to change his or her attitude or condition on the basis of the information and to focus his or her energy on proper matters since, according to research results, people get nervous or expend their energy unknowingly on second-rate matters.

These objects are achieved on the basis of the characterizing features set forth in the appended claims.

For example, a belt to be worn around the chest monitors the user's physical condition on the basis of sensors or transducers included therein and, in the presence of an abnormal or unfavourable condition, produces just a sound signal and/or transmits the message further to a wrist-held monitor used for delivering numerical or graphic data to the user. If the device is provided with a wireless remote communication, an alarm indicating a hazardous condition can also be forwarded with prior known technology automatically to an alarm center. The user him- or herself can also induce a manual alarm by means of a press key provided for the purpose. The transducers can also be located in such a manner that some of the transducers are included in the wrist unit and some in the belt worn around the chest, whereby the wrist unit transmits an anomalous message to the unit held around the chest, which analyzes the received information together with information provided by its own transducers and sets off an alarm or a sound signal thereabout and, if necessary, carries it forward in a wireless fashion. The feasible transducers include movement transducers such as acceleration transducers, temperature, conductivity transducers or sensors and prior known heart rate detecting techniques. A stripped-down wrist unit can be used for providing a mere stress indicator, which informs its user by a sound signal and/or a display. In this case, the transducer comprises a multiple transducer, designed by using the film technology and having movement, temperature and conductivity transducers polymerized or plasma-sputtered therein.

BRIEF DESCRIPTION OF THE DRAWINGS

The invention will now be described in more detail with reference made to the accompanying drawings, in which.

DETAILED DESCRIPTION OF THE PREFERRED EMBODIMENT

Figure 1B:
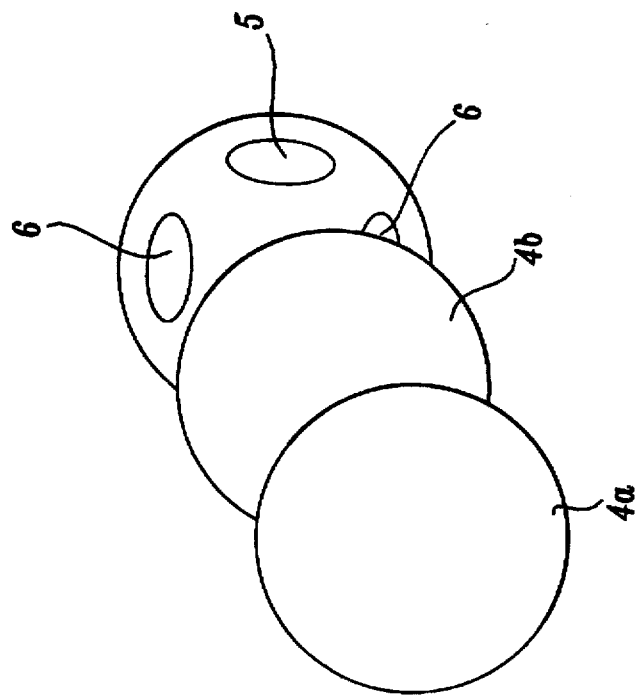
FIG. 1 shows a wrist-held display and detector unit and the design of a multiple detector transducer included therein.
Figure 1A:
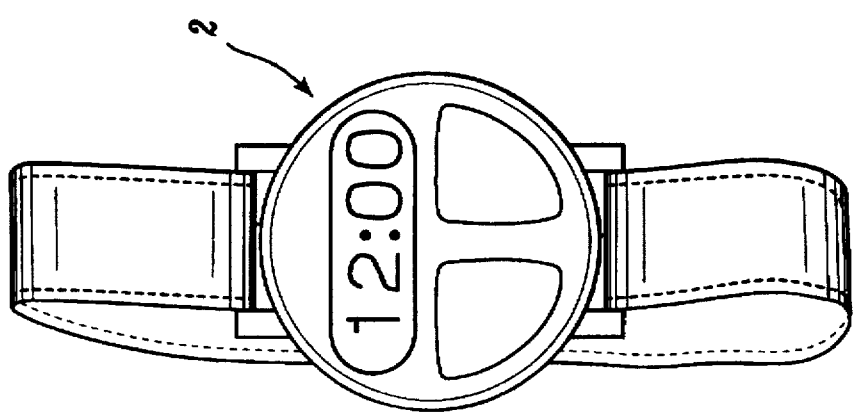

A device of the invention only includes a detector and transducer unit 1 fastenable to some part of the body and/or a wrist-held display and detector unit 2. The body-held detector and transducer unit 1 may include a heart rate detector 3 and/or a movement transducer 4 such as an acceleration transducer, temperature transducer 5 and a conductivity transducer 6, which are in contact with the skin of a user. The transducer unit 1 may include a belt 8 to be worn around the chest. The wrist unit 2 may include just a display and sound signal device as well as a communication unit for a wireless communication with the transducer unit 1. The wrist unit 2 can also be provided with some of the transducers 3–6 in view of performing some of the necessary analysis. The wrist unit 1 may include e.g. all transducers required for the surveillance of performance condition and, thus, its operation can be concentrated on a user. In the illustrated case, the wrist unit 1 has its back face fitted with flexible polyester films, in which transducers are made by polymerization or plasmasputtering. A film 4a serves as a semiconducting coating for a movement transducer, a film 4b as a conducting coating for a movement transducer, and the top layer is a film including a temperature transducer 5 and a skin conductivity transducer 6. A remote receiver 7 includes a wireless receiver and a control output for the further transmission of an alarm.

The transducers 3–6 are monitored by means of a microprocessor 9, which uses its algorithm to provide a description of the health or physical condition and/or performance condition of a user by using a plurality of different transducer signals to compensate for false data caused by an individual transducer. A characterizing feature in the signal processing is that it takes into consideration a combined effect of the motoric activity and biophysical indicators as well as the heart rate of a user when producing a description of the physical condition of a user. That is, by monitoring the interrelations between various indicators and by compensating the anomalies caused by various performance conditions of a body in the analyzing process, it is possible to provide a substantially more reliable description than that obtained by traditional methods. Typically, it has been customary to monitor e.g. just the heart rate and to detect anomalies occurring therein. The analyzing process of the invention is capable of detecting whether a higher heart rate results from motoric activity or e.g. from a sudden attack of illness with no motoric activity observed. Another characterizing feature is the identification of successive manifestations of various motoric activities, whereby e.g. falling down and the following unconsciousness can be detected by means of a movement or acceleration transducer as well as by the observation of heart rate. When the device is only used for monitoring the level of performance condition (e.g. stress), an error caused by motoric activity can be compensated for and, thus, the device can be used continuously notwithstanding the physical performance level.

The multiple transducer 4–6 used as a transducer is also a characterizing feature in the invention. It includes a polymerized or plasma-sputtered movement, temperature and conductivity transducer designed by a film technique on the surface of the transducer unit 1 whenever the wrist unit 2 is not in operation or when the wrist unit 2 only functions as a display and detector unit.

I claim:

1. A body-held monitoring device for a physical condition and/or a performance condition, comprising:

a plurality of transducers each measuring various quantities indicating a physical condition and/or a performance condition, the plurality of transducers including a multiple detector transducer designed by a film technique;

wherein the transducers are monitored by means of a microprocessor that provides information indicating the physical condition and/or performance condition of a monitored person in such a manner that a comparison of a plurality of different transducer signals is used to compensate for an anomaly from an individual transducer;

a body-held transducer unit having a skin-contacting surface carrying at least some of the transducers; and a wrist-held display and detector unit from which the information indicating a physical condition and/or performance condition is obtainable by means of a display and/or a sound signal.

2. A device as set forth in claim 1, wherein the multiple detector transducer is provided with polymerized or plasma-sputtered temperature and skin conductivity transducers.

3. A device as set forth in claim 1, wherein the microprocessor for processing the transducer signals is included in the body-held transducer unit.

4. A device as set forth in claim 3, wherein the transducer unit is provided with a two-way wireless communication link with the wrist-held display and detector unit.

5. A device as set forth in claim 1, wherein the microprocessor is set for continuous surveillance of a performance condition, the information indicating a performance condition being obtainable from the display and detector unit continuously or whenever desired.

6. A body-held monitoring device for a physical condition and/or a performance condition, comprising:

a plurality of transducers each measuring various quantities indicating a physical condition and/or a performance condition, the plurality of transducers including a multiple detector transducer designed by a film technique;

a body-held transducer unit fastenable to the body and having a skin-contacting surface carrying at least some of the plurality of transducers;

a microprocessor that provides information indicating the physical condition and/or performance condition of a monitored person in such a manner that a comparison of a plurality of different transducer signals is used to compensate for an anomaly from an individual transducer; and a display and detector unit in wireless communication with the transducer unit and from which the information indicating a physical condition and/or a performance condition is obtainable by means of a display and/or a sound signal.

7. A device as set forth in claim 6, wherein the display and detector unit is a wrist-held unit including at least one of the plurality of transducers and is provided with a two-way wireless communication link with the transducer unit.

\* \* \* \* \*

UNITED STATES PATENT AND TRADEMARK OFFICE
CERTIFICATE OF CORRECTION

PATENT NO. : 5,670,944
DATED : September 23, 1997
INVENTOR(S) : Matti Myllymaki

Figure 2:
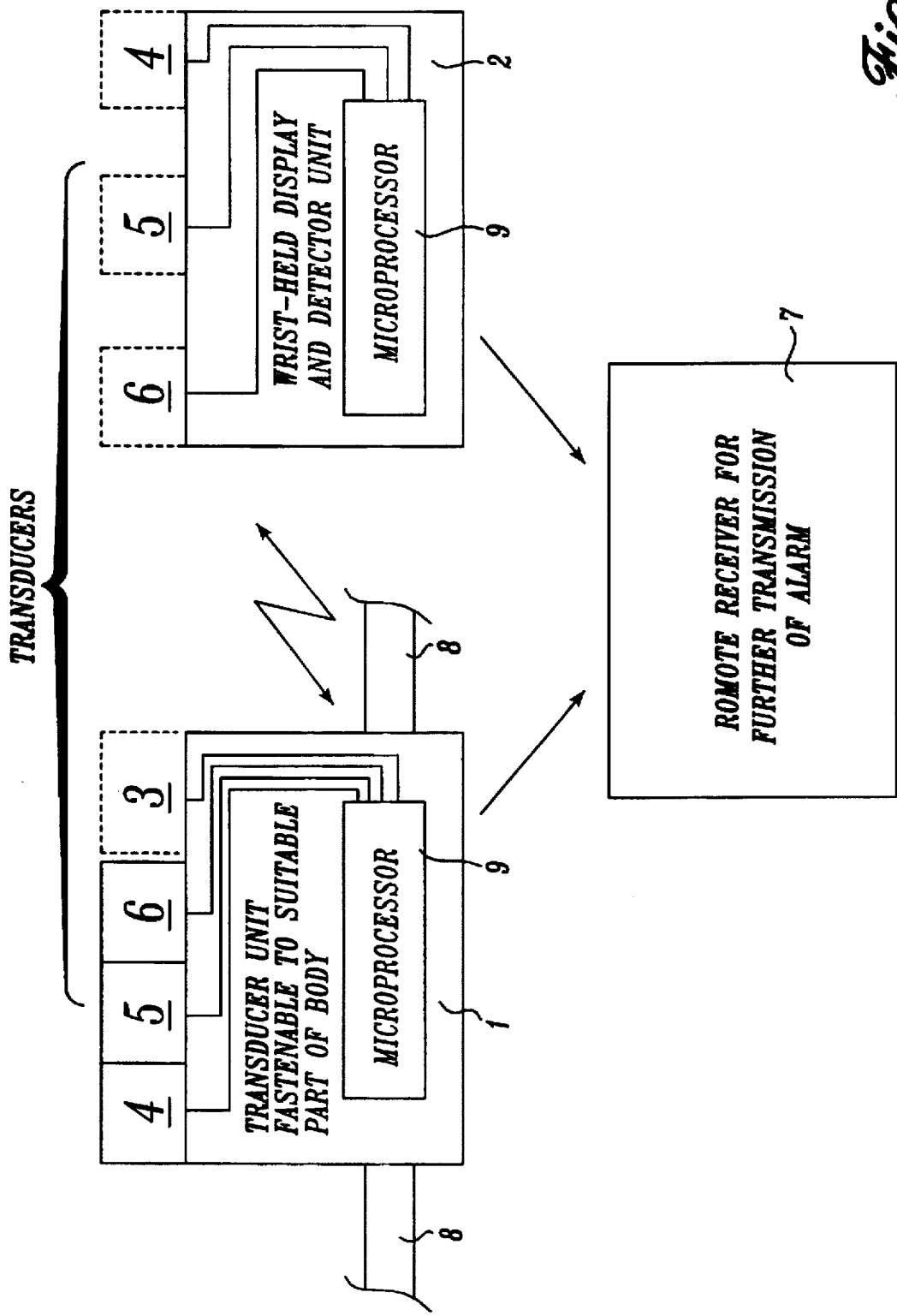
FIG. 2 shows a general block diagram for a device of the invention.
Figure 2:
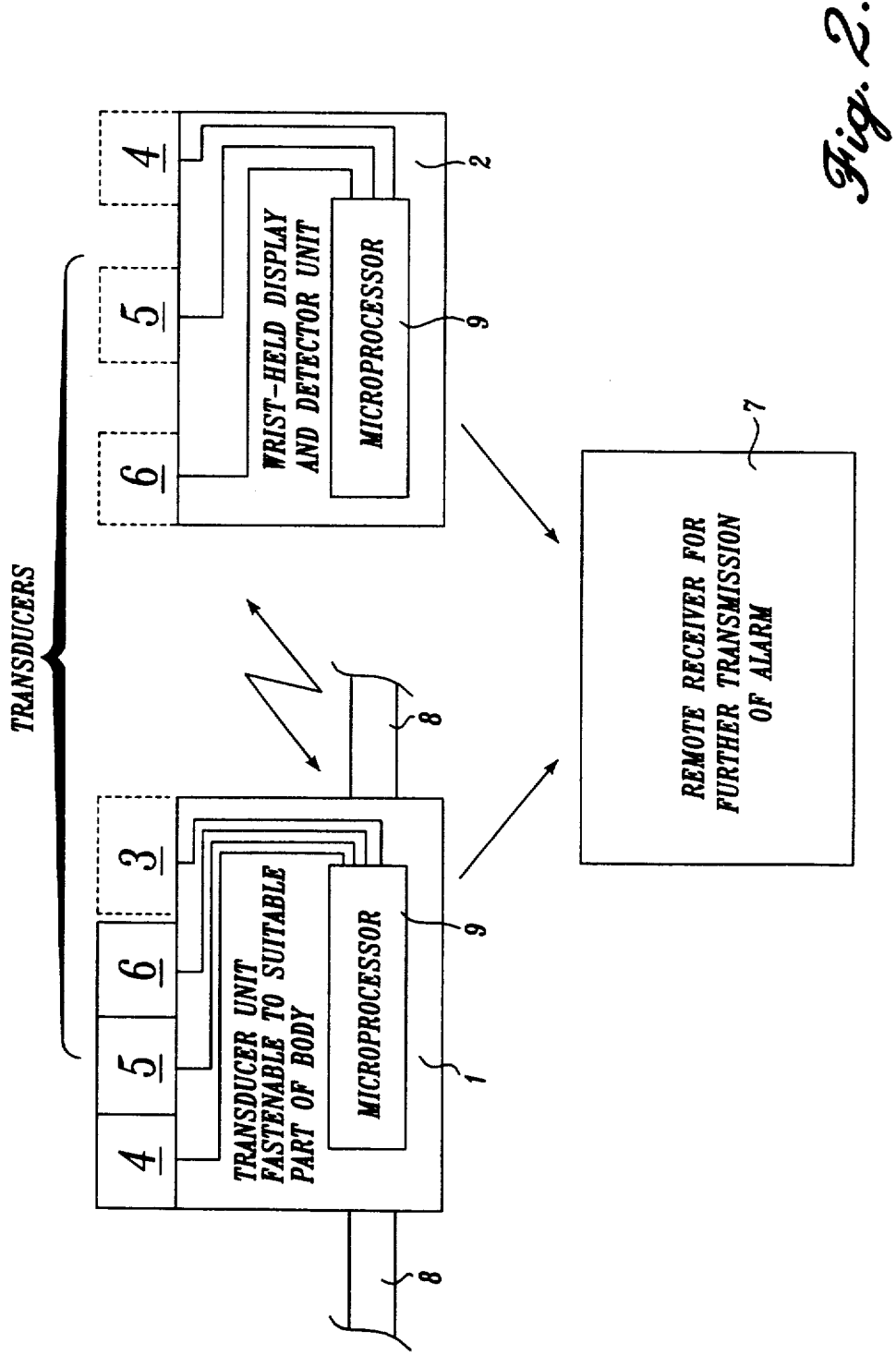

It is certified that error appears in the above-identified patent and that said Letters Patent is hereby corrected as shown below:

| COLUMN | LINE | ERROR |
|---|---|---|
| Drawings Figure 2 | Sheet 2 of 2 | "ROMOTE RECEIVER FOR FURTHER TRANSMISSION OF ALARM" should read --REMOTE RECEIVER FOR FURTHER TRANSMISSION OF ALARM-- |

Signed and Sealed this

Twenty-fourth Day of March, 1998

BRUCE LEHMAN

Attest:

Attesting Officer

Commissioner of Patents and Trademarks